United States Patent [19]

Klippel

[11] 4,259,950
[45] Apr. 7, 1981

[54] EXTRICATION BACK BRACE
[75] Inventor: Allen P. Klippel, Omaha, Nebr.
[73] Assignee: Rescue Products, Inc., St. Louis, Mo.
[21] Appl. No.: 18,159
[22] Filed: Mar. 7, 1979
[51] Int. Cl.³ .......................... A61F 5/04; A61F 13/00
[52] U.S. Cl. .................................... 128/89 R; 128/90; 128/134
[58] Field of Search .................... 128/134, 87 B, 87 C, 128/75, 78, 89 R, 133; 5/82, 90, 84 R, 84 C

[56] References Cited

U.S. PATENT DOCUMENTS

| | | | |
|---|---|---|---|
| 2,102,069 | 0/1937 | Hanicke | 128/87 B |
| 3,449,776 | 0/1969 | Brock | 5/82 |
| 3,737,923 | 0/1973 | Prolo | 128/78 |

Primary Examiner—Robert W. Michell
Assistant Examiner—C. W. Shedd
Attorney, Agent, or Firm—Gravely, Lieder & Woodruff

[57] ABSTRACT

An adjustable extrication back brace for stabilizing the pelvic area, the wings or illiac crest, the shoulder area and the head so that the spine related to these portions of an accident victim's body can be held in a neutral position before substantial movement can or should be undertaken to remove the victim from the accident scene and in which the back brace comprises cooperating corrugated panels slidably interrelated for longitudinal adjustment, a cervical block positionable on one panel to fit the cervical curve, and a plurality of securing strap anchors spaced along the panels for retaining the victim in position with the back brace aligned against the vetertrael spine or mid-line of the back. The back brace panels are made small to be maneuvered into position where space and the body position makes access difficult.

8 Claims, 5 Drawing Figures

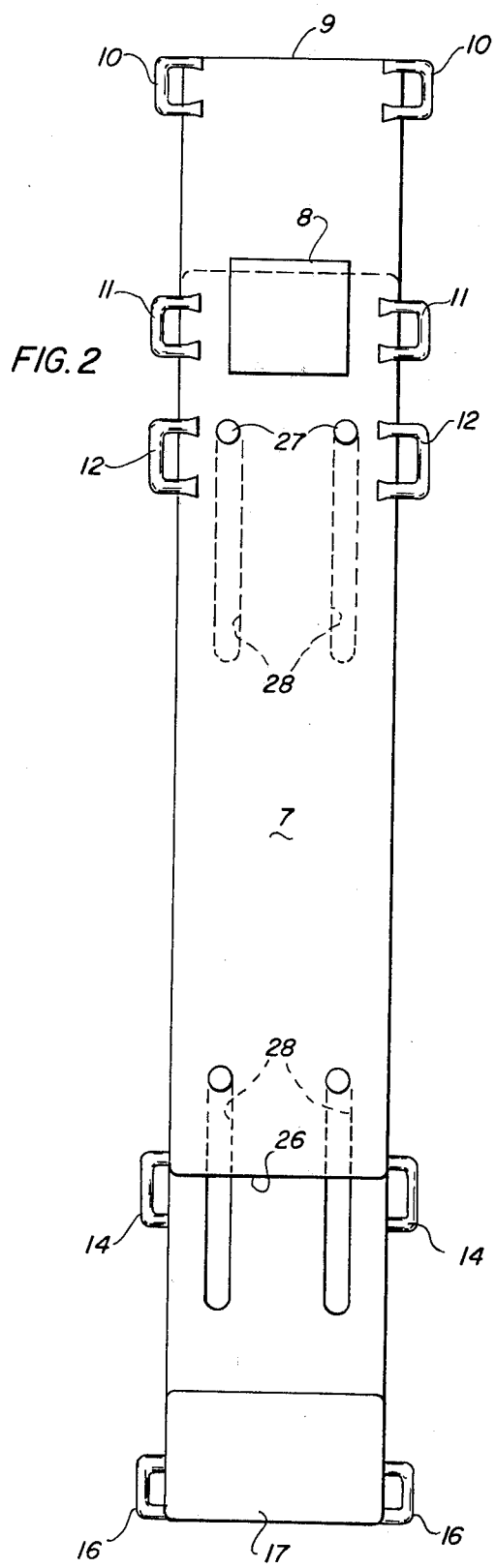
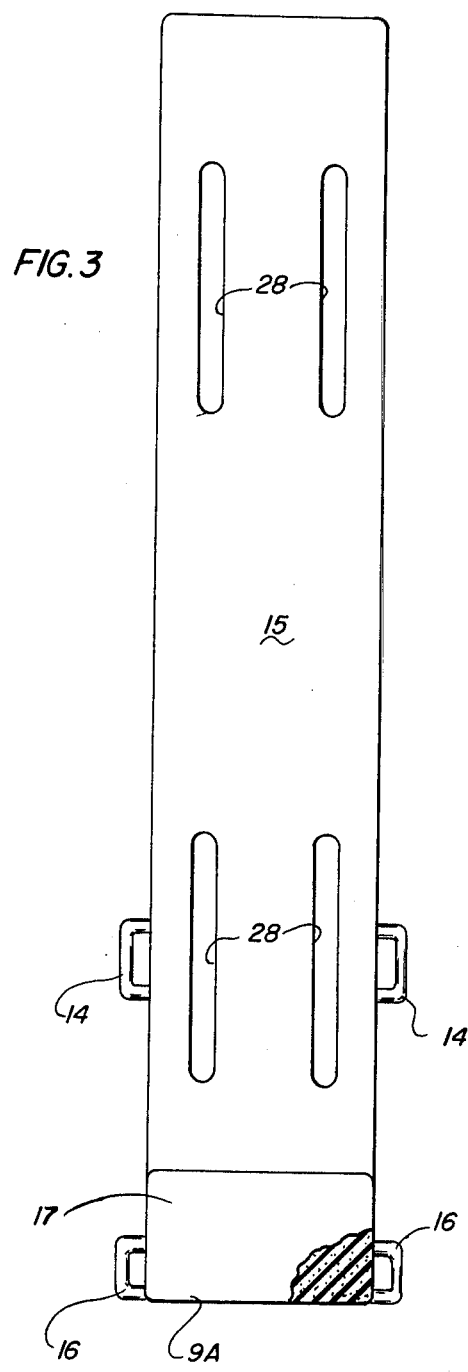

EXTRICATION BACK BRACE

BACKGROUND OF THE INVENTION

An accident victim may have sustained injuries that vary from minor to very serious, but because of problems of on the spot diagnosis it is better to suspect more serious injury than appears on quick inspection and proceed accordingly. The serious injuries are usually associated with head, neck and spine damage, any of which could result in permanent after effects if the victim is improperly handled at the accident scene.

Devices have been provided for assisting removal of accident victims from the location where found. Such devices usually take the form of splints, orthopedic stretchers, backboards, and similar means for immobilizing the victim during removal from the accident area and during transportation to a place for proper medical examination and treatment. The orthopedic stretcher is a device for enabling emergency medical technicians to slide the stretcher halves under a victim for subsequent movement while in the position in which found, thus minimizing the possibility of complicating the original injury.

BRIEF DESCRIPTION OF THE INVENTION

The present invention is concerned with an extrication back brace having novel structural characteristics for expanding the utility thereof.

The objects of the invention are to provide a back brace capable of being adjusted to fit substantially all people, to provide a back brace that possesses dimensional characteristics enabling it to be used in difficult areas where a victim may be found, to provide a back brace which possesses mechanical strength to immobilize a victim and especially the head and spine areas, and to provide a back brace permitting the victim to lie flat and without tipping or rolling.

Other objects of the invention will be brought out in the following description which pertains to an adjustable extrication back brace having fitting means for fitting the same to various sizes of accident victims, and including means for stabilizing the head, neck, shoulder area, spine and pelvic area of an accident victim. In addition to the foregoing objects, the present invention is adaptable to usefulness in applying the same to a victim while in the position in which found and before any attempt is made to move the victim from the accident scene.

BRIEF DESCRIPTION OF THE DRAWINGS

The present improved extrication back brace is shown in a preferred embodiment in the following illustrative views, wherein:

FIG. 2 is a view similar to FIG. 1 but with the back brace extended to its ultimate length;

FIG. 3 is a plan view of the bottom panel of the back brace to reveal details thereof;

DETAILED DESCRIPTION OF THE PREFERRED EMBODIMENT

Figure 1:
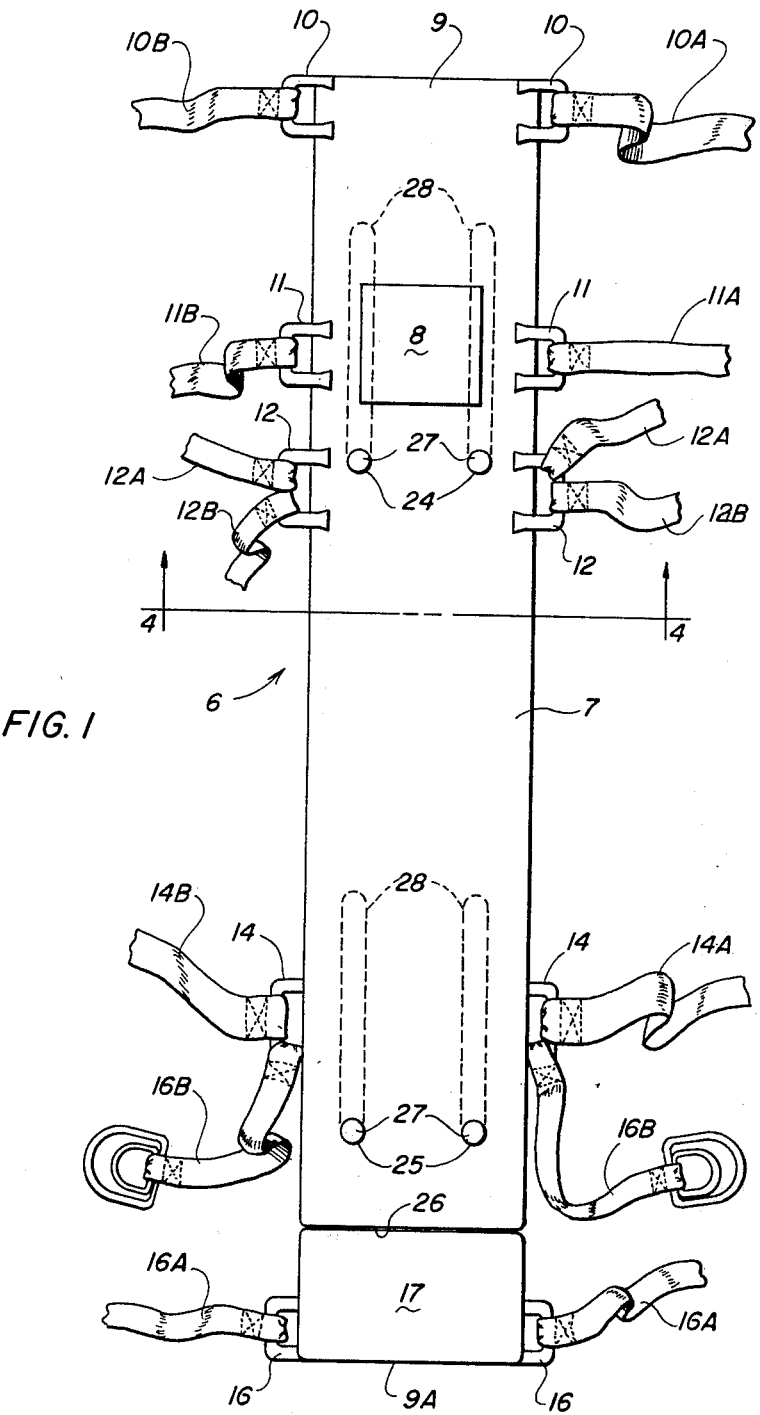
FIG. 1 is a top plan view of the back brace with the top and bottom panels in the collapsed position and with the retention straps opened out at each side.
Figure 4:
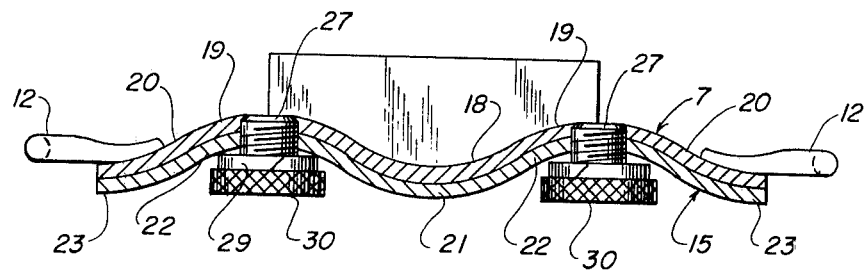
FIG. 4 is a sectional elevation of the back brace as seen along line 4—4 in FIG. 1 to reveal certain details thereof.

Reference will now be made to the various views in the accompanying drawings which have disclosed a presently preferred embodiment of the present invention. In FIG. 1 it can be seen that the back brace 6 is presented in its retracted or collapsed position for convenient storage until it is needed. The upper panel 7 of the back brace is provided with a cervical block 8 located adjacent what will be referred to as the head end 9 of the panel 7. The opposite longitudinal margins of the panel 7 are provided with suitable securing means which include pairs of strap anchors 10, 11 and 12 spaced there along with the anchors 10 adjacent the head end 9, so as to be in a position for aligning cooperating retention straps 10A and 10B to secure the victim's forehead against the panel 7. The pair of anchors 11 are located in position to permit the securing straps 11A and 11B to cooperate in holding a cervical collar 13 (See FIG. 5) in position surrounding and substantially immobilizing the victim's head and neck, with the cervical block 8 aiding in the proper support of the neck area. The pair of anchors 12 are located so as to be in positions where securing straps 12A and 12B can be applied around the victim's shoulder and return through the armpit area without traversing the chest area so as to avoid impairing or restricting respiration.

The back brace is further provided with paired anchors 14 which are secured on opposite sides of the panel 15, whereby securing straps 14A and 14B attached to the anchors 14 may be secured in cooperation to immobilize the hip or illiac crest of the accident victim. A further pair of anchors 16 attached to the lower panel 15 serve as anchors for straps 16A which separately pass under the victim and are run through the crotch so as to cooperate with and attach to straps 16B which are fastened to the anchors 14 adjacent the anchors 16. In connection with the utilization of the securing straps 16A and 16B it should be understood that the upper panel 7 is not as long as the lower panel 15 for the purpose of exposing a portion at the bottom end 9A of the back brace in order to mount thereon a block of padding 17 which has a thickness somewhat greater than the thickness of the upper panel 7 so as to prevent contact with the adjacent edge of the panel 7.

The improved back brace includes certain novel structural characteristics which are best seen by comparing FIGS. 1 through 4 inclusive. The back brace includes the upper panel 7 and a cooperating nested lower panel 15 which in cross section are corrugated to provide an upwardly facing channel or longitudinal valley 18 for accurate alignment of the spine of the accident victim. The valley 18 is located between raised ribs or crests 19 and the crests are directed outwardly to terminate at flanges or lateral wings 20 to which certain of the respective anchors are secured, such as anchors 10, 11 and 12. It can be appreciated that the bottom back brace panel 15 has a similar valley 21, crests 22 and flanges or lateral wings 23 for engaging the panel 7 in nested relation and the corrugated form prevents tipping or rolling because the flanges 23 become effective to prevent such reaction. The upper panel 7 is formed with apertures 24 in the area aligned with the anchors 12, and with additional apertures 25 located near the bottom end 26 of the upper panel. Each of these apertures is adapted to receive a threaded stud 27, with the upper end of each stud flush with the rib or crest area 19 of the upper panel 7. The respective studs 27 project through elongated slots 28 formed in the underlying rib or crest areas 22 of the bottom panel 15. Each stud 27 is adapted to receive a suitable lock washer 29 and a knurled nut 30 which is effective when threaded up on the stud to draw the spine board panels 7 and 15 together after sliding them out to whatever degree of extension is found necessary to match the dimensions of the accident victim. As shown in FIG. 2 the bottom back brace panel 15 is shown in its ultimate extension position so that the respective studs 27 are now at the opposite ends of the elongated slots 28 from the view of FIG. 1, and the padding 17 is spaced from the end 26 of the upper panel 7.

Figure 5:
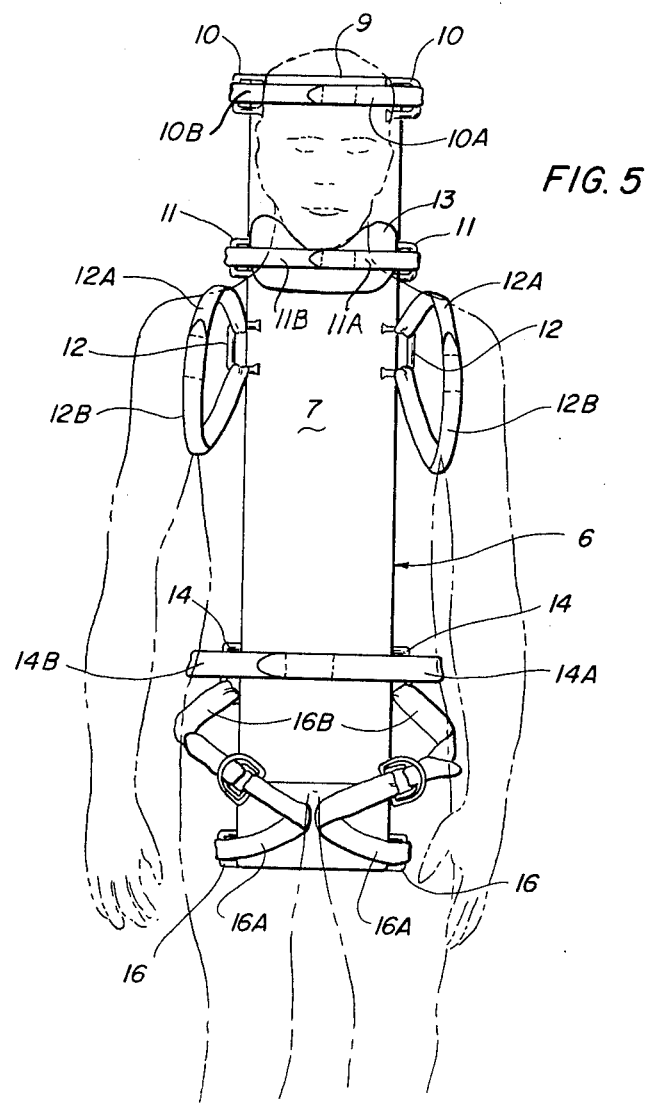
FIG. 5 is a schematic view of the back brace in position when applied to an accident victim, and showing how the same is secured in position to render it effective for the intended purposes.

FIG. 5 illustrates the application of the back brace to an accident victim, the victim being shown in dotted outline. In this case a cervical collar 13 is shown and is intended to be installed around the neck of the victim prior to securing the back brace. This will enable the straps 11A and 11B to be applied around the exterior of the cervical collar 13, and with the ends of these straps secured together by the use of Velcro retainer means. It is also shown that the straps 10A and 10B are applied to retain the forehead of the victim on the upper panel 7 and suitably cradled in the valley 18 near the head end 9. It is evident that the unique corrugated configuration of the back brace panels performs the highly important function of centering the head and neck in normal alignment, and this alignment is maintained by the anchor straps 10A and 10B as well as the straps 11A and 11B. In order to achieve substantial immobilization of the shoulders of the victim straps 12A and 12B at each anchor 12 are provided so that strap 12A may be looped over the shoulder and straps 12B may be brought up through the respective armpits to engage straps 12A at Velcro retainer means. Thus the back brace is secured at the shoulders without affecting breathing.

The panel 15 can be extended out from panel 7 by releasing the several nuts 30 so that the back brace can be adjusted as to length until the straps 14A and 14B are aligned at the waist. Thereafter the nuts 30 are tightened to fix that adjustment. The corrugated cross section configuration of the panel 15 allows the nuts 30 and studs 27 to be located in the bottom facing crests 22 where they are out of the way and reasonably safe from accidental release. Finally, the straps 16A and 16B at each side are carried out upon extension of the panel 15 so that they may be looped around each leg and through the crotch for retaining the adjacent body in position.

The presently improved back brace may be formed of suitable material such as non-magnetic material to enable x-ray examination, and to provide a light-weight structure. The corrugated cross sectional configuration of each of the panels provides substantial strength and resistance to torsion which is highly desirable to stabilize the spinal area of an accident victim. It has been pointed out that the back brace is intended to be manueverable into limited space areas, and for that purpose a preferred structure may be dimensioned, for example so as to have a width to length ratio of one to five. It is preferred that the upper panel may have actual dimensions to which the width is six inches and the length is somewhat shorter than the bottom panel to allow for suitable size padding 17. The lower or bottom panel may have identical dimensional characteristics as to width.

The foregoing specification has set forth the dimensional and structural characteristics of the extrication back brace which is capable of having a minimum dimension when in its storage or collapsed position and may be extended to selected positions and secured by easily manipulated threaded means which are disposed in places where they will not protrude or get in the way. It is believed that the foregoing description will provide a basis for recognizing that variations may be made without departing from the intent of this improvement. As an example, in FIGS. 1 and 5 D-ring securing means have been illustrated for retaining the straps 16A and 16B in the position shown in FIG. 5. It is, of course, understood that the Velcro retainer means for joining the ends of the other securing straps may also be used in place of the D-rings in view of the ability to adjust the Velcro retainer means more quickly than adjusting the D-rings.

What is claimed is:

1. In a back brace a pair of panels, each having a substantially centered longitudinally extending valley disposed between and parallel with longitudinally extending crests raised at each side of said valley, said valley and crests being segments of curved surfaces and said crests having laterally extending and downwardly and laterally outwardly directed flanges forming opposite longitudinal margins of said panels, and said panels being nested with said valleys and crests in overlying relation, said pair of panels having means located in said crests for permitting extension of one panel relative to the other such that said pair of panels may slide relative to each other so as to assume a first shortened telescoped position and other positions in which said panels are moved to predetermined extension positions, said last means including longitudinally directed slots in one panel and cooperating elements on said other panel projecting through said slots, releasible clamping means engaged on said elements for securing said pair of panels in said first position and in said predetermined extension positions, and flexible means carried by said pair of panels in positions for securing said panels to the head and torso of a person, whereby the head and torso of a person is substantially immobilized with the spine stabilized in said valley between said crests.

2. The back brace of claim 1 in which said releasible clamping means for securing said panels in said positions is positioned at the underside of said crests, whereby said clamping means is recessed between said flanges and the underside of said valley.

3. The back brace of claim 1 in which said pair of panels have a width to length ration of substantially one to five.

4. The back brace of claim 1 in which cervical support means is positioned in the valley of one of said panels and spaced closer to one end thereof than the other end.

5. In a back brace a pair of elongated panels having a corrugated configuration in cross section and assuming a storage position in which a top one of said panels is carried in a position on top of the other panel constituting the bottom panel, said corrugations including curved surfaces forming a central upwardly facing valley and reversely curved surfaces forming crests along each side and each crest terminating in a marginal flange such that in operative position of application to the human body the valley is aligned with the spine and said crests are alignable at each side of the spine, slots formed in said bottom panel and extending longitudinally thereof with remote ends of said slots being spaced inwardly from the opposite ends of said bottom panel and with the other ends of said slots being in spaced relation from each other, guide means secured on said top panel in position to engage in and project through said slots in said bottom panel for keeping said panels in alignment upon longitudinal sliding movement out of storage position to a predetermined extended position within the length of said slots, and securing means engaged on said guide means in position to abut with said bottom panel for retaining said panels selectively in a stored or extended position within the limits of said slots.

6. The back brace of claim 5 in which said valley, crests and marginal flanges extend throughout the length of said pair of panels, and said panels have substantially a width to length ratio of one to five.

7. The back brace of claim 5 in which securing means is disposed adjacent one end of said top panel in position to engage the forehead of an accident victim, other securing means, including a cervical block is spaced inwardly from said one end and is positioned to engage adjacent the neck area of the accident victim, and further securing means is spaced from said other securing means in position to retain the accident victim at the shoulder and armpit area, all of said securing means include anchor elements fastened outwardly of and to the opposite flanges of said top panel.

8. The back brace of claim 5 in which said elongated panels have substantially the same width, said bottom one of said nested panels is longer that said top panel for exposing a portion of said bottom panel surface, and padding means is secured to said exposed surface portion, said exposed portion being utilized in the extended position to support the illiac crest of the accident victim.

* * * * *